(12) United States Patent
Banerjee et al.

(10) Patent No.: US 6,346,516 B1
(45) Date of Patent: Feb. 12, 2002

(54) CATIONIC AMPHIPHILES CONTAINING N-HYDROXYALKYL GROUP FOR INTRACELLULAR DELIVERY OF BIOLOGICALLY ACTIVE MOLECULES

(75) Inventors: Rajkumar Banerjee; Prasanta Kumar Das; Gollapudi Venkata Srilakshmi; Nalam Madhusudhana Rao; Arabinda Chaudhuri, all of Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/275,817

(22) Filed: Mar. 25, 1999

(30) Foreign Application Priority Data

Nov. 9, 1998 (IN) ........................ 3325/DEL/98
Nov. 9, 1998 (IN) ........................ 3327/DEL/98
Nov. 9, 1998 (IN) ........................ 3324/DEL/98

(51) Int. Cl.$^7$ ..................... A61K 31/13; A61K 31/14; A61K 31/70
(52) U.S. Cl. .................. 514/44; 514/546; 514/552; 514/642; 514/667; 514/669; 514/851; 554/108; 554/109; 554/110; 560/252; 560/253; 564/292; 564/503; 564/506
(58) Field of Search .................. 564/503, 506, 564/292; 514/667, 669, 851, 642, 552, 44, 546; 560/252, 253; 554/108, 109, 110

(56) References Cited

U.S. PATENT DOCUMENTS 4,897,355 A  *  1/1990  Eppstein et al. ......... 435/240.2

FOREIGN PATENT DOCUMENTS

EP  0 842 652  *  5/1998
JP  61-37892  *  2/1986

OTHER PUBLICATIONS

Nehashi et al. Chem. Abstr. 106:215917, 1987.*
Devinsky et al. Chem. Abstr. 129:340830, 1998.*

* cited by examiner

Primary Examiner—Peter O'Sullivan
(74) Attorney, Agent, or Firm—Finnegan, Henderson, Farabow, Garrett & Dunner, L.L.P.

(57) ABSTRACT

The present invention provides novel cationic amphiphiles containing novel N-hydroxyalkyl group and therapeutic formulations containing the said amphiphiles that are capable of facilitating transport of biologically active molecules into cells. The said novel cationic compounds having the following structural formula:

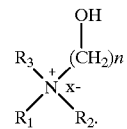

25 Claims, 7 Drawing Sheets

Figure 1:
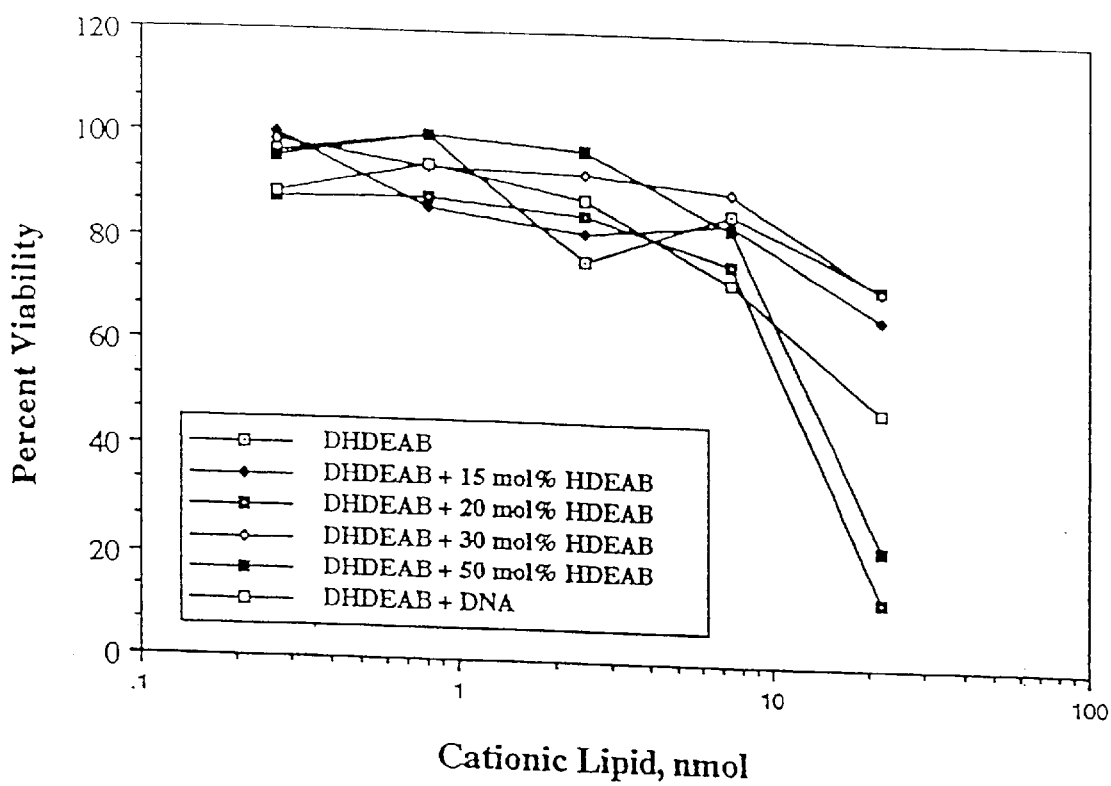

CATIONIC AMPHIPHILES CONTAINING N-HYDROXYALKYL GROUP FOR INTRACELLULAR DELIVERY OF BIOLOGICALLY ACTIVE MOLECULES

FIELD OF THE INVENTION

The present invention relates to novel cationic amphiphiles containing novel N-hydroxyalkyl group and therapeutic formulation containing the said amphiphiles that are capable of facilitating transport of biologically active molecules into cells. The invention further provides a process for the preparation of the said thereapeutic formulation containing amphiphilic compounds. The novel cationic amphiphiles containing N-hydroxyalkyl group of this invention are potentially useful to deliver therapeutically effective amounts of biologically active molecules into the cells of mammals. The area of medical science that is likely to benefit most from the present invention is gene therapy.

BACKGROUND OF THE INVENTION

In gene therapy, patients carrying identified defective genes are supplemented with the copies of the corresponding normal genes. However, genes (DNA), the polyanionic macromolecules and the cell surfaces of the biological membranes both being negatively charged, spontaneous entry of normal copies of genes into the target cells of patients is an inefficient process (because of electrostatic repulsion). This is why the past decade has witnessed an unprecedented upsurge of global interest in developing efficient gene delivery reagents for introducing normal genes into the target cells of patients suffering from various genetic (inherited) diseases such as cystic fibrosis, Gaucher's illness, Fabry's disease etc. Many gene delivery reagents (also known as transfection vectors) including retrovirus, adenovirus, and cationic amphiphilic compounds (i.e. compounds containing both polar and non-polar functionalities) are being used as the carriers of polyanionic genes in combating hereditary diseases in gene therapy. The amphiphilic nature (presence of both polar and non-polar regions in the molecular structures) of the compounds designed to deliver therapeutically actives molecules, ensures smooth interaction of these carrier molecules with the polar and non-polar regions of plasma membranes, compartments within the cells and the biologically active molecules itself. At physiological pH, the cationic amphiphiles in the form of liposomes or micelles associate favorably with the negatively charged regions of the macromolecular polyanionic DNA enhancing the intracelluar uptake of the resulting complex between the cationic lipids and the negatively charged DNA. Reproducibility, high degree of targetability and low cellular toxicity are increasingly making the cationic amphiphiles the transfection vectors of choice in gene therapy.

Reported Developments

An impressive number of cationic lipids with varying structures have been reported for the intracellular delivery of therapeutically active molecules as exemplified by the following references:

Felgner et al., *Proc. Natl. Acad. Sci. U.S.A.,* 84, 7413–7417 (1987), reported the first use of a highly efficient cationic lipid N-[1-(2,3-dioleyloxy)propyl]-N,N,N-trimethyl ammonium chloride (DOTMA) as the DNA transfection vector.

U.S. Pat. Nos. 4,897,355 and 4,946,787 (1990) reported the synthesis and use of N-[.omega..(.omega.-1)-dialkyloxy]- and N-[..omega..(.omega.-1)-dialkenyloxy]-alk-1-yl-N,N,N-tetrasubstituted ammonium amphiphiles and their pharmaceutical formulation as efficient transfection vectors.

Leventis, R. and Silvius, J. R. *Biochim. Biophys. Acta.* 1023, 124–132, (1990) reported the interactions of mammalian cells with lipid dispersions containing novel metabolizable cationic amphiphiles.

U.S. Pat. No. 5,264,618 (1993) reported the synthesis and use of additional series of highly efficient cationic lipids for intracellular delivery of biologically active molecules.

Felgner et al. *J Biol. Chem.* 269, 2550–2561 (1994) reported enhanced gene delivery and mechanistic studies with a novel series of cationic lipid formulations.

U.S. Pat. No. 5,283,185 (1994) reported the synthesis and use of 3β[N-(N$^1$,N$^1$-dimethylaminoethane)carbamoyl] cholesterol, termed as "DC-Chol" for delivery of a plasmid carrying a gene for chloramphenicol acetyl transferase into cultured mammalian cells.

U.S. Pat. No. 5,283,185 (1994) reported the use of N-[2-[[2,5-bis[(3-aminopropyl)amino]-1-Oxopentyl]aminoethyl]-N,N-dimethyl-2,3-bis-(9-Octadecenyloxy)-1-Propanaminium tetra(trifluoroacetate), one of the most widely used cationic lipids in gene delivery. The pharmaceutical formulation containing this cationic lipid is sold commercially under the trade name "Lipofectamine".

Solodin et al. *Biochemistry* 34, 13537–13544, (1995) reported a novel series of amphiphilic imidazolinium compounds for in vitro and in vivo gene delivery.

Wheeler et al. *Proc. Natl. Acad.Sci. U.S.A.* 93, 11454–11459, (1996) reported a novel cationic lipid that greatly enhances plasmid DNA delivery and expression in mouse lung.

U.S. Pat No. 5,527,928 (1996) reported the synthesis and the use of N,N,N,N-tetramethyl-N,N-bis(hydroxy ethyl)-2,3-di(oleolyoxy)-1,4-butanediammonium iodide i.e. pharmaceutical formulation as transfection vector.

U.S. Pat. No. 5,698,721 (1997) reported the synthesis and use of alkyl O-phosphate esters of diacylphosphate compounds such as phosphatidylcholine or phosphatidylethanolamine for intracellular delivery of maromolecules.

U.S. Pat. Nos. 5,661,018; 5,686,620 and 5,688,958 (1997) disclosed a novel class of cationic phospholipids containing phosphotriester derivatives of phosphoglycerides and sphingolipids efficient in the lipofection of nucleic acids.

U.S. Pat. No. 5,614,503 (1997) reported the synthesis and use of an amphipathic transporter for delivery of nucleic acid into cells, comprising an essentially nontoxic, biodegradable cationic compound having a cationic polyamine head group capable of binding a nucleic acid and a cholesterol lipid tail capable of associating with a cellular membrane.

U.S. Pat. No. 5,705,693 (1998) disclosed the method of preparation and use of new cationic lipids and intermediates in their synthesis that are useful for transfecting nucleic acids or peptides into prokaryotic or eukaryotic cells. These lipids comprise one or two substituted arginine, lysine or ornithine residues, or derivatives thereof, linked to a lipophilic moiety.

U.S. Pat. No. 5,719,131 (1998) has reported the synthesis of a series of novel cationic amphiphiles that facilitate transport of genes into cells. The amphiphiles contain lipophilic groups derived from steroids, from mono or dialkylamines, alkylamines or polyalkylamines.

Although the above mentioned cationic lipids have been successfully exploited for the intracellular delivery of genes, the efficiencies for the intracellular uptake procedures are insufficient and need to be improved. The transfection activities of most of the above mentioned cationic lipids are modest and therefore substantial quantities of these cationic lipids must be consumed. The associated cellular toxicities of the lipids and the metabolites thereof are, thus naturally, issues of concern. Accordingly, demands for developing new class of cationic amphiphiles with high transfection efficiencies and low cellular toxicities continue in this field of art.

OBJECTS OF THE INVENTION

The main objective of the invention is to provide novel cationic amphiphilic compounds containing non-toxic N-hydroxyalkyl group.

Another objective of the invention is to provide novel cationic amphiphilic compounds, which are useful for delivery of therapeutically effective amounts of biologically active molecules into cells/tissues of mammals.

Yet another objective of the invention is to provide cationic amphiphilic compounds such that a hydrophobic group is either directly linked to the positively charged Nitrogen atom or is linked to the said Nitrogen atom via an ester or methylene group.

Still another objective of the invention is to provide novel cationic amphiphilic compounds with at least one hydroxyalkyl group containing 1–3 carbon atoms directly linked to the positively charged Nitrogen atom.

Yet another objective of the invention is to provide novel cationic amphiphilic compounds without any glycerol backbone in their structure.

Another objective of the invention is to provide novel therapeutic formulation comprising one or more of the cationic amphiphilic compounds of the invention.

It is a further objective of the invention to provide therapeutic formulation useful in gene therapy and delivery of biologically active molecules into cells/tissues of mammals.

It is yet another objective to provide for intravenous administration of the therapeutic formulation for targeting organs for gene therapy.

DETAILED DESCRIPTION OF THE INVENTION

The present invention relates to novel cationic amphiphiles containing N-hydroxyalkyl group. The novel cationic amphiphiles containing N-hydroxyalkyl group of this invention are potentially useful to deliver into the cells of patients therapeutically effective amounts of biologically active molecules. The area of medical science that is likely to benefit most from the present invention is gene therapy.

Cationic amphiphiles disclosed in the present invention possess several novel structural features. These features may be seen in comparison with, for example, cationic amphiphilic structures such as those disclosed in Felgner et al. *J Biol. Chem.*, 269, 2550–2561 (1994), a representative structure of which is 1,2-dimyristyloxypropyl-3-dimethyl-hydroxyethyl ammonium bromide ("DMRIE") and to those disclosed by Bennett et al. *J. Med. Chem.*, 40, 4069–4078 (1997), a representative structure of which is N,N-[Bis(2-hydroxyethyl)]-N-methyl-N-[2,3-bis(tetradecanoyloxy) propyl] ammonium chloride ("DMDHP").

The following distinctive structural features are common to the cationic amphiphiles disclosed in the present invention: (1) the presence of a hydrophobic group which is either directly linked to the positively charged nitrogen atom or is linked to the positively charged nitrogen via an ester group, (2) the presence of at least one hydroxyalkyl group containing 1–3 carbon atom that is directly linked to the positively charged nitrogen atom and (3) unlike many other glycerol-based cationic amphiphiles, the cationic transfection lipids disclosed in the present invention do not have any glycerol backbone in their molecular architecture. It is believed that these unique structural features contribute significantly to the increased transfection efficiencies of the cationic amphiphiles disclosed herein. The enhanced in vitro transfection efficiencies of N,N,-di-[O-hexadecanoyl] hydroxyethyl-N-hydroxyethyl-N-methylammonium bromide (DOHEMAB) and N,N-di-n-hexadecyl-N,N-dihydroxyethylammonium bromide (DHDEAB), the two novel transfection lipids of the present invention, is compared to Lipofectamine, the most widely used commercially available highly efficient transfection lipid.

According to the practice of the present invention, "cationic" means the positive charge is either on a quatemized nitrogen atom or on a protonated tertiary nitrogen atom. The cationic characters of the amphiphiles may contribute to the enhanced interaction of the amphiphiles with biologically active molecules (such as nucleic acids) and/or with cell constituents such as plasma membrane glycoproteins. Such enhanced interaction between the cationic transfection lipid and the biological by active molecules and/or cell membrane constituents may play a key role in successfully transporting the therapeutic molecules into the cells.

The cationic amphiphiles of the present invention have certain common structural and functional groups. As such, the said cationic amphiphilic compounds may be represented by the following generic formula:

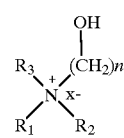

Wherein
n is an integer between 1 and 3
$R_1$ may be H, saturated or unsaturated aliphatic group $(C_8–C_{20})$ or long chain saturated or unsaturated alkyl group $(C_7–C_{19})$.
$R_3$ may be hydroxyalkyl group of 1–3 carbon atoms,
$R_2$ may be a long chain saturated alkyl group $(C_7–C_{19})$ or $((CH_2)_n$—Z—$(C_7–C_{19}))$
Z may be methylene group (—$CH_2$), or an esteric group (—O—CO—)
X is either a halogen atom or tosylate group.

Various novel amphiphilic compounds having the above basic structural formula may be synthesised by the processes described in co-pending U.S. patent application Ser. No. 09/275,816 (Indian Application No.3324/DEL/98, 3325/DEL/98 and 3327/DEL/98 all dated Nov. 9$^{th}$, 1998). The cationic amphiphiles disclosed in the present invention share certain common structural features as discussed herein below. Further, in the said amphihpiles the preference of $C_8–C_{20}$ is specifically low because below the chain length of $C_8$ the amphiphiles loose the aggregation property and the specific reason for not using carbon chains longer than $C_{20}$ is because they are not compatible with biological membranes in terms of their lengths. Further, the additional linking groups that may be practised within the scope of this invention include —O-(ether) CONH-(amide) group etc. Among the three different linking groups described in the invention herein below, the esteric group is most preferred.

Further, the products obtained during the synthesis of the said amphiphilic compounds are hydrolysis products. The moleclues were so constructed to aid in their breakdown within a cell subsequent to performing the task of transfection. The structure of the amphiphiles may also be altered by a combination of alkyl and amine moieties, which structures would fall within the teachings and scope of the present invention. Such modifications are apparent to those skilled in the art. Accordingly, certain representative amphiphilic compounds that may be practiced within the scope of the invention are described hereinbelow, along with their respective structural formulae: Accordingly, the invention provide cationic amphiplies represented by the following structural formula (1):

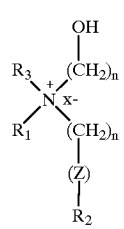
(I)

wherein
n is an integer between 1 and 3;
$R_1$ represents either H or a saturated aliphatic group;
Z represents a methylene (—$CH_2$—) group;
$R_2$, independently, represents a long-chain saturated alkyl group (from $C_7$ to $C_{19}$);
$R_3$ is a small hydroxyalkyl group consisting of 1–3 carbon atoms;
X is either a halogen atom or a tosylate group.

In one preferred embodiment of the cationic lipids, when n is 2, $R_1$ is selected from H or $C_8$ to $C_{20}$ saturated alkyl groups, $R_2$ is selected from $C_7$ to $C_{19}$ saturated alkyl groups, $R_3$ is hydroxyethyl group (—$CH_2$—$CH_2$—OH) and X is selected from Br and Cl.

In one preferred embodiment n=2; Z=$CH_2$; $R_3$ is 2-hydroxylethyl group; $R_1$ is selected from the n-$C_{14}H_{39}$ to n-$C_{20}H_{41}$. $R_2$ is selected from n-$C_{11}H_{23}$ to n-$C_{17}H_{35}$ and X is selected from Br or Cl. According to this aspect of invention, particularly effective amphiphile includes, for example, NN-di-n-hexadecyl-N,N-dthydroxyethylammonium bromide (DHDEAB, amphiphile No. 1).

In another preferred embodiment, n=2; Z=$CH_2$; $R_3$ is 2-hydroxyethyl group; $R_1$ is H and $R_2$ is selected from the n-$C_{11}H_{23}$ to n-$C_{17}H_{35}$. According to this aspect of invention, particularly effective amphiphile would include, for example, N-n-hexadecyl-N,N dihydroxyethylammonium bromide (HDEAB, amphiphile No. 2).

The said pair of particularly effective representative cationic amphiphiles N,N-di-n-hexadecyl-N,N-dihydroxyethylammonium bromide (DHDEAB), amphiphile No 1 and N-n-hexadecyl-N,N-dihydroxyethylammonium bromide (HDEAB), amphiphile No. 2 are represented by the following structural formulae:

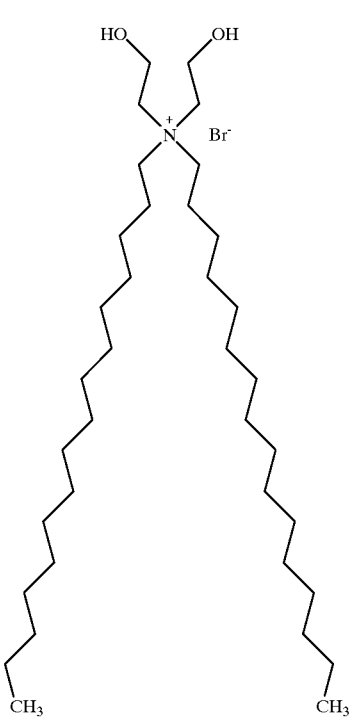
1

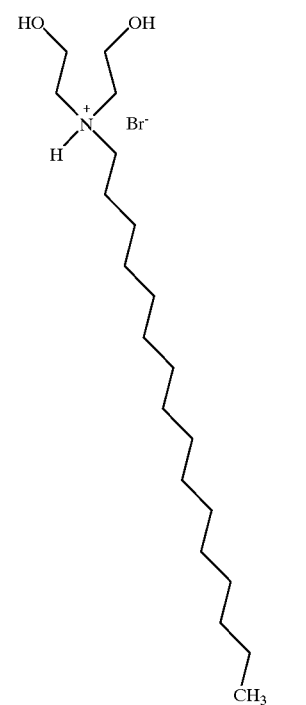
2

Accordingly the invention provides cationic amphiphiles having structural formula (II) as represented hereunder:

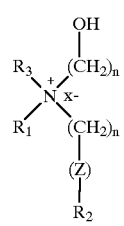
(II)

wherein:

n is an integer between 1 and 3;

$R_1$ independently, represents either a saturated aliphatic group or an unsaturated aliphatic group (from $C_8$ to $C_{20}$): Z represents a methylene (—$CH_2$—) group;

$R_2$ independently, represents a long-chain saturated alkyl group (from $C_7$ to $C_{19}$);

$R_3$ is a small alkyl group (from $C_1$ to $C_3$);

X is either a halogen atom or a tosylate group.

In one preferred embodiment, when n is 2, $R_1$ is selected independently from $C_8$ to $C_{20}$ saturated or unsaturated alkyl groups, $R_2$ is selected from $C_7$ to $C_{19}$ saturated alkyl groups, $R_3$ is selected from small alkyl groups (from $C_1$ to $C_3$) and X is selected from Br and Cl.

In a preferred embodiment, n=2; Z=$CH_2$, $R_3$ is selected from methyl or ethyl group; $R_1$ is selected from the $C_{14}H_{27}$ to $C_{20}H_{39}$, $R_2$ is selected from n-$C_{12}H_{23}$ to n-$C_{17}H_{35}$ and X is selected from Br or Cl. According to this aspect of invention, particularly effective amphiphile includes, for example, N-methyl-N-n-octadecyl-N-oleyl-N-hydroxyethylammonium chloride (MOOHAC, amphiphile No. 3)

In a further preferred embodiment, n=2, Z=$CH_2$ $R_3$ is selected from methyl or ethyl group; $R_1$ is selected from the n-$C_1H_{29}$ to n-$C_{20}H_{41}$, $R_2$ is selected from n-$C_1H_{23}$ to n-$C_{12}H_{35}$ and X is selected from Br of Cl. According to this aspect of invention, particularly effective amphiphile includes, for example, N,N-di-n-octadecyl-N-methyl-N-dihydroxyethylammonium chloride (DOMHAC, amphiphile No. 4)

According to an embodiment, an effective representative pair of cationic transfection lipids include, for example, N-methyl-N-n-octadecyl-N-oleyl-N-hydroxyethylammonium chloride (MOOHAC), amphiphile No 3 and N,N-di-n-octadecyl-N-methyl-N-dihydroxyethylammonium chloride (DOMHAC), amphiphile No. 4 represented by their structural formulae as under:

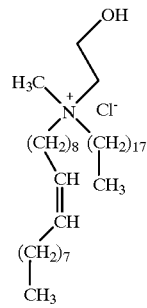
3

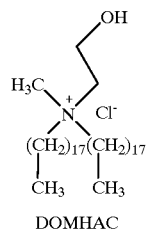
4
DOMHAC

Additionally, the present invention provides novel cationic amphiphiles that facilitate the intracellular delivery of biologically active molecules, said amphiphiles having the structural formula (III).

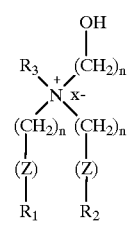
(III)

wherein:

n is an integer between 1 and 3, Z an ester group (—O—CO—) and $R_1$ and $R_2$ independently, represent a long-chain saturated or unsaturated alkyl group (from $C_7$ to $C_{19}$), $R_3$ can be either a small alkyl group ($C_1$ to $C_3$) and X is either a halogen atom or a tosylate group, In an embodiment of the invention, n=2; Z=O—CO—; $R_3$ is selected from methyl or ethyl group; $R_1$ is selected from the n-$C_{14}H_{29}$ to n-$C_{20}H_{41}$, $R_2$ is selected from n-$C_{14}H_{29}$ to n-$C_{20}H_{41}$ and X is selected from Br or Cl. According to this aspect of invention, particularly effective amphiphile includes, for example, NN-di(O-hexadecanoyl/hydroxyethyl-N-hydroxyethyl-N-methylammoniun bromide (DOHEMAB, amphiphile No. 5).

According to this aspect of the invention, a particularly effective representative cationic transfection lipid includes N,N,-di[O-hexadecanoyl]hydroxyethyl-N-hydroxyethyl-N-methylammoniun bromide (DOHEMAB), amphiphile 5 having the structural formula:

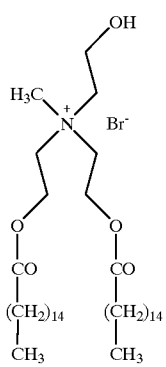

Formulations

The invention also provides novel therapeutic formulation comprising therapeutically effective amounts of the cationic amphiphilic compounds disclosed in the present invention, biologically active molecules and co-lipids. One or more additional physiologically acceptable substances may be included in the pharmaceutical formulation of the invention to stabilize the formulation for storage or to facilitate successful intracellular delivery of the biologically active molecules.

Co-lipids

Co-lipids, according to the practice of the invention are useful in mixing one or more cationic amphiphiles. These co-lipids would include cholesterol, N-n-hexadecyl-N, N-dihydroxyethyl ammonium bromide (HDEAB) and the like. A preferred range of molar ratio of cationic amphiphile to co-lipid is about 1:0 to 1:2.5. As such, it is within the art to vary the said range to a considerably wide extent.

Biologically active molecules that can be administered intracellularly in therapeutic amounts using the amphiphilic compounds of the invention include:
a) Ribosomal RNA
b) Antisense polynucleotide of RNA or DNA
c) Polynucleotide of genomic DNA, cDNA or mRNA that encodes for a therapeutically important protein.

The cationic amphiphiles of the invention may be blended such that one or more representatives thereof may be used in a combination to facilitate entry of the said biologically active molecules into cells/tissues.

In a further embodiment, the amphiphiles may be used either in pure form or in a combination with other lipids or amphiphiles such as helper lipids which may include phospholipids namely, cholesterol, phosphatidylethanolamine, phosphatidylglycerol etc.

In a further embodiment, the said therapeutic formulation may be stored at 0° C.–4° C. until complexed with the nucleic acid. Agents that prevent bacterial growth and increase the shelf life may be included along with agents that stabilize the preparation e.g., low concentrations of glycerol. It is specifically warned that freezing and thawing cycles could cause loss in efficiency of the formulation.

In another embodiment, the formulation of amphiphiles and nucleic acid may be administered intravenously besides other routes such as intramuscular and intra peritonial. Further, the said formulation of amphiphiles may be administered to cells at a ratio of 0.1–0.5 microgram of DNA to 50,000 cells in an in virto system. The amount of amphiphile could be varied from a charge ratio of 0.1 to 10, considering one positive charge for one amphiphile molecule, to one charge of nucleotide base.

The plasmid used is a construct of an Rous Sarcoma virus promoter linked to a reporter gene β-galactosidase as given in the method of Banos et al (Developmental Biology 127, 209–219 (1988)). The plasmid could be of any construction and the example given is merely to demonstrate the efficiency of the amphiphilic formulation. Similar examples of plasmid include PGL-2 and PGL-3 of Promega and others.

The invention further provides a process for the preparation of the said formulation, comprising the steps of: preparing a dispersion of a cationic amphiphile disclosed in the present invention; contacting said dispersion with a biologically active molecule to form a complex between said amphiphiles and said molecule and contacting cells with said complex thereby facilitating transfer of said biologically active molecules into the cells.

In an embodiment, the invention provides a method for the treatment of cystic fibrosis and related diseases comprising the steps of administering therapeutically effective amount of the said formulation to a subject in need thereof.

In another embodiment, the said formulation may be administered through intravenous, intramuscular and intraperitonial routes.

BRIEF DESCRIPTION OF THE ACCOMPANYING DRAWINGS

Figure 2:
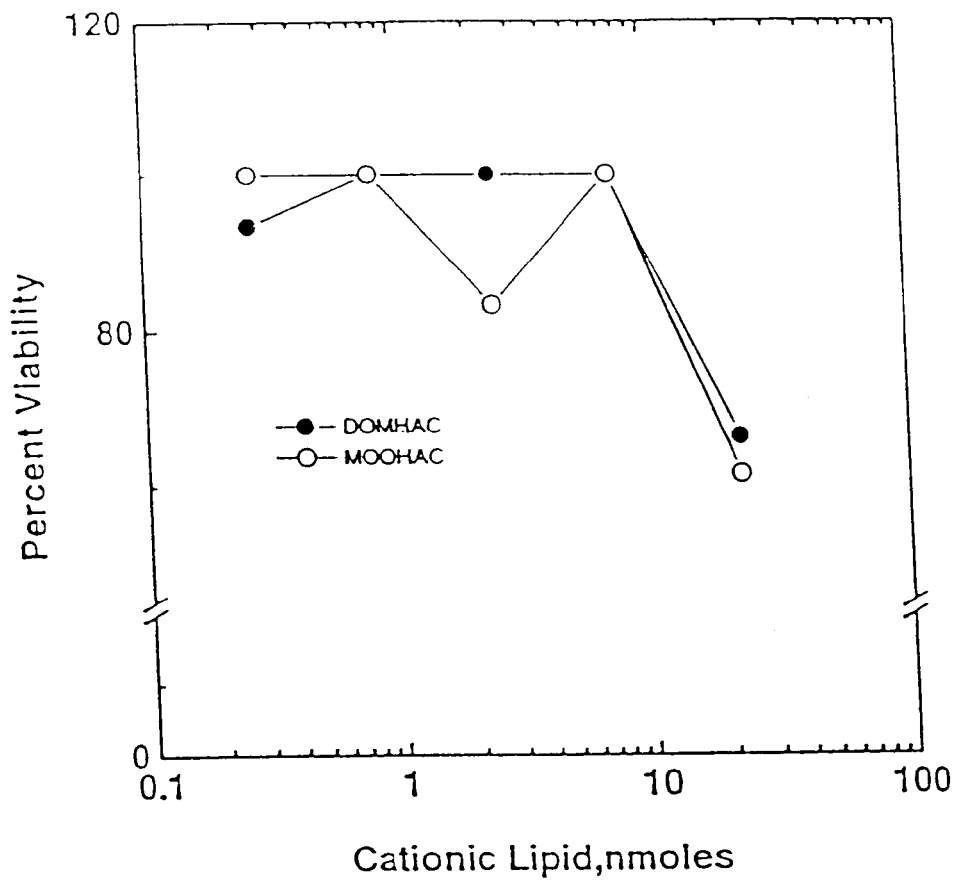

FIGS. 1 and 2 provide the in vitro cellular toxicities of the cationic amphiphiles disclosed in the present invention.

FIGS. 3–7 provide in vitro transfection efficiencies for the cationic amphiphiles disclosed in the present invention and that of Lipofectamine, the most widely used commercially available transfection lipid, under certain conditions.

FORMULATIONS CONTAINING THE CATIONIC AMPHIPHILES OF THE INVENTION AND THE IN VITRO ADMINISTRATION THEREOF

Figure 3:
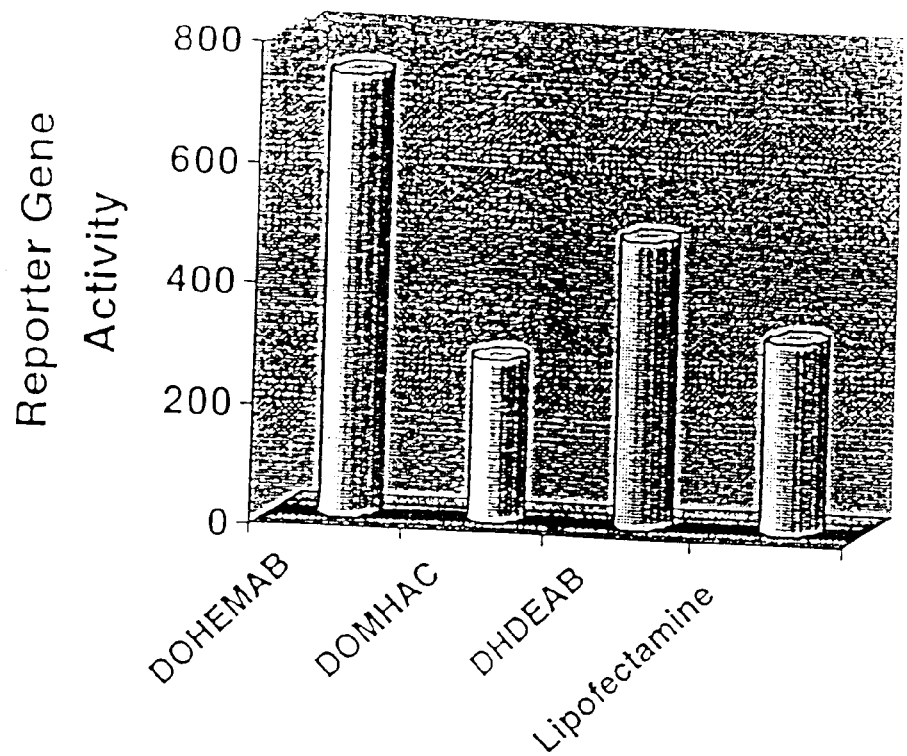
Figure 4:
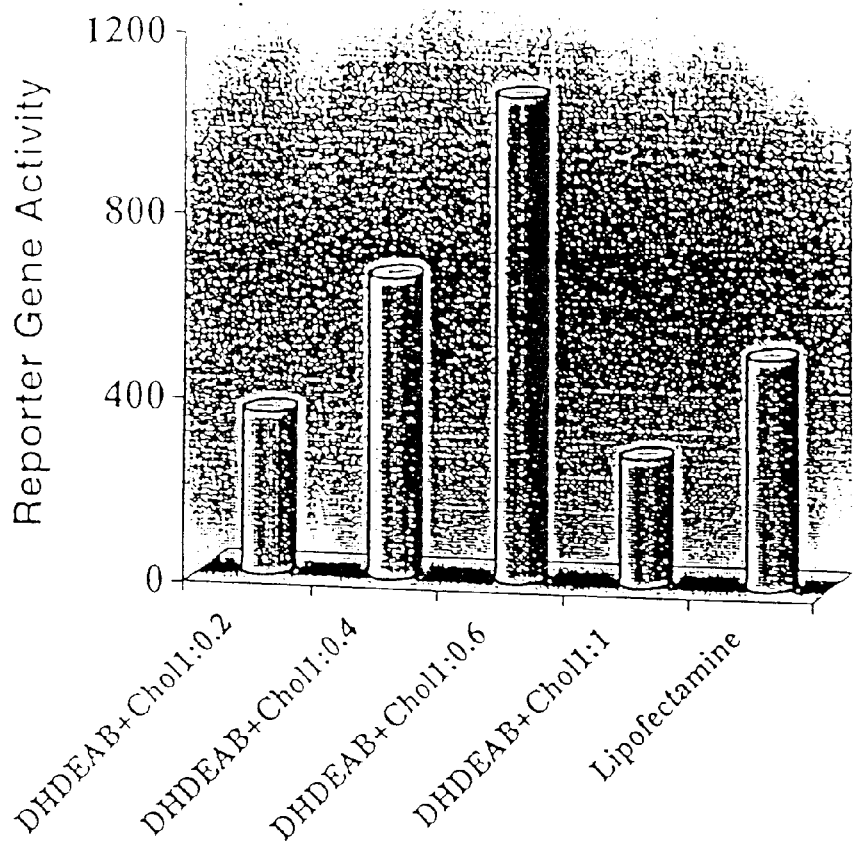
Figure 5:
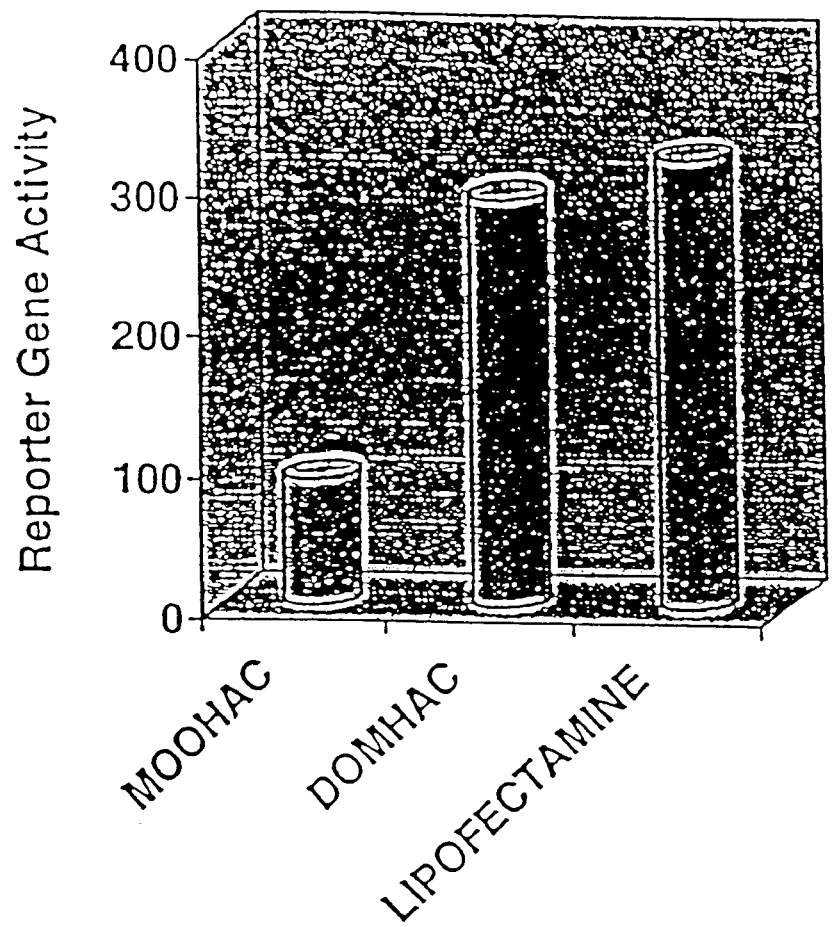
Figure 6:
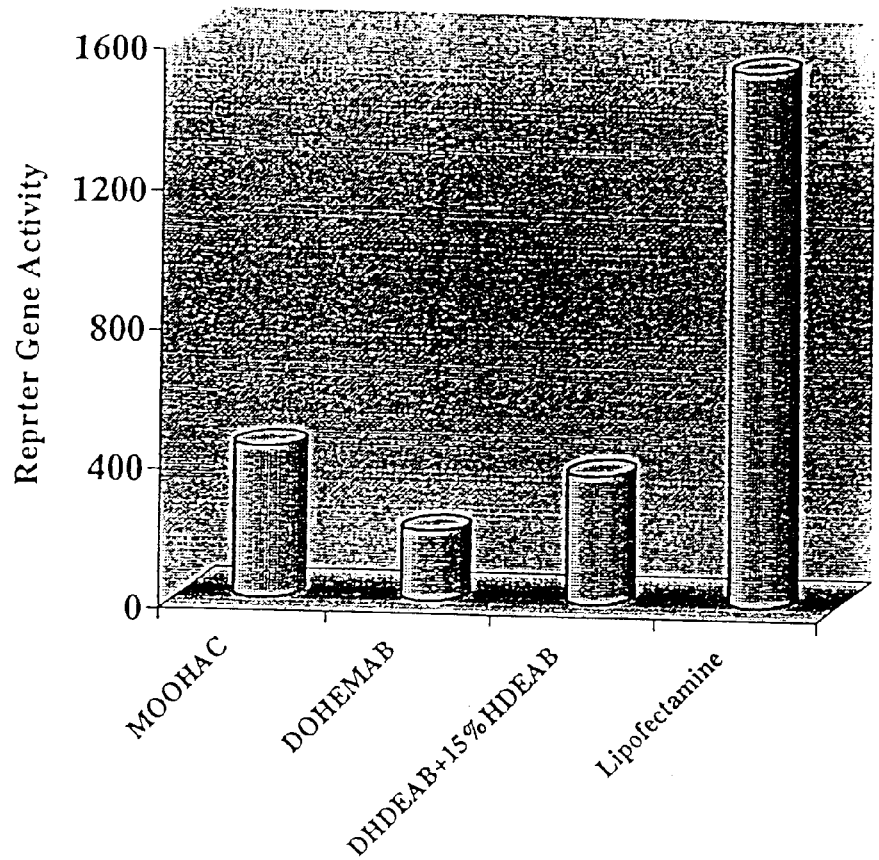
Figure 7:
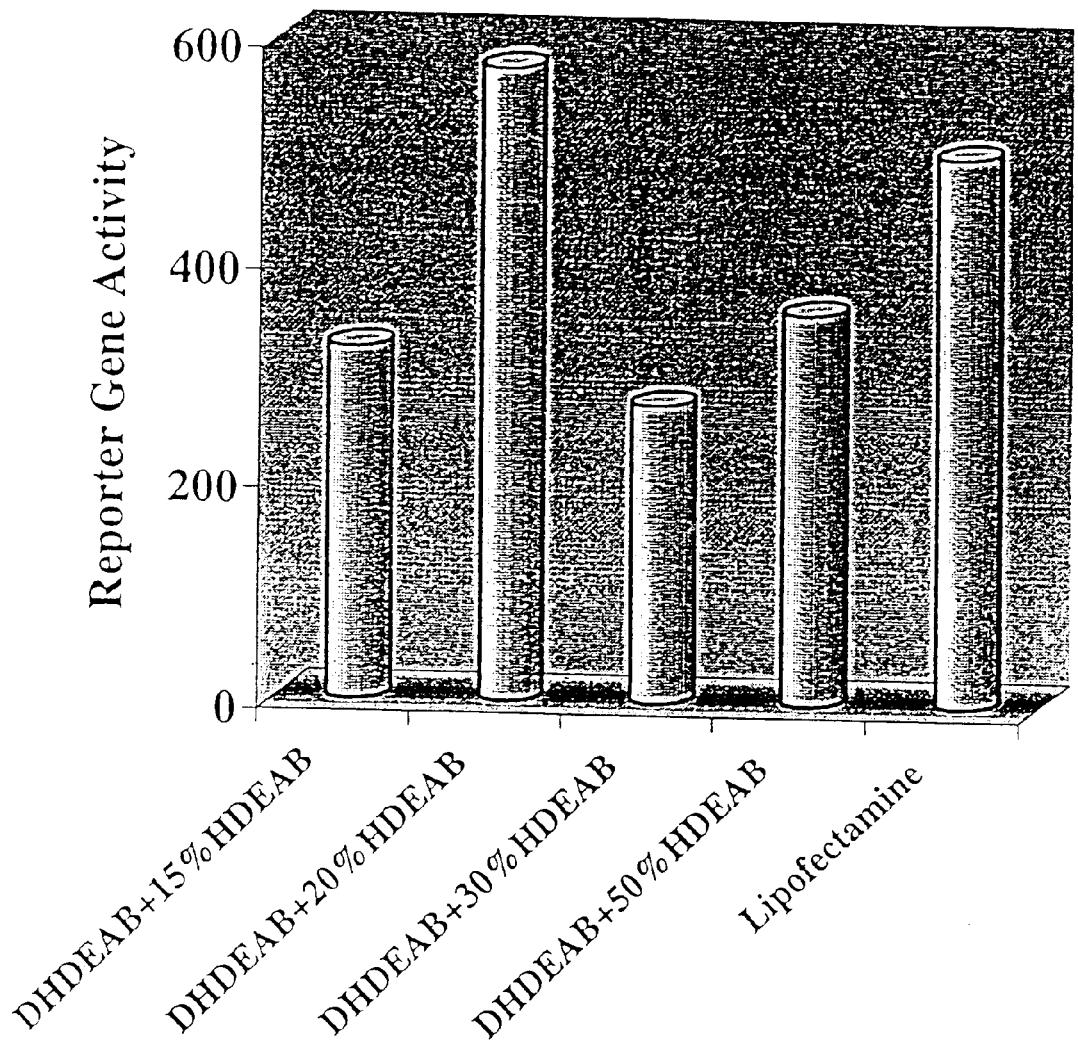

The present invention also provides for various formulations that facilitate intracellular delivery of biologically active molecules. The formulations of the transfection lipids disclosed herein were prepared either by keeping the amount of the cationic amphiphiles constant at 1 mM and varying the amounts of the auxiliary neutral lipid (cholesterol) within the range 0.2 mM to 1 mM or by adding varying amounts of the novel single-chain auxiliary cationic lipid N-n-hexadecyl-N,N-dihydroxyethylammonium bromide (HDEAB) within the range of 0.15 mM–0.5 mM to a mixture containing 1 mM of cholesterol and 1 mM twin-chain novel cationic amphiphiles disclosed herein. As shown in FIG. 3 of the drawings accompanying this specification, combination of 1 mM DHEAB and 0.6 mM Cholesterol is a highly efficient formulation. Similarly, FIG. 4 of the drawings accompanying this specification shows an additional highly effective formulation containing 0.2 mM HDEAB, 1 mM DHEAB and 1 mM Cholesterol.

CELLULAR TOXICITIES OF THE CATIONIC AMPHIPHILES DISCLOSED IN THE INVENTION

The viabilities of cells in presence of various cationic amphiphiles disclosed herein were checked according to the standard protocol described in "Animal Cell Culture. 2nd Edition. Ed. I.R.L Press t, Oxford University Press (1997)". The transfection efficiencies of the cationic lipids were studied in the range of 0–10 nmole and within this limit, the cell toxicities were observed to be minimal and the cell viabilities were determined to be more than 80% as summarized in FIGS. 1 and 2. The cationic amphiphiles of FIG. 1 were used at a concentration of 1 mM together with 1 mM cholesterol as the neutral co-lipid.

THE MAIN ADVANTAGES OF THE PRESENT INVENTION

1. The procedures for making these novel cationic amphiphiles being simple, the prices of this new transfection reagent should be remarkably lower than that of LIPOFECTAMINE™ and LIPOFECTIN.™
2. The transfection efficiency of the novel cationic amphiphiles are much better than that of LIPOFECTIN™ and comparable to or better than the transfection efficiencies of LIPOFECTAMINE.™
3. The cationic amphiphiles disclosed in the present invention have been tested positive for transfecting COS 1, Hela, Vero, CV 1 and NIH3T3 cells and the primary cell line, Rat Skin Fibroblasts.

The following examples are given by way of illustration of the present invention and therefore should not be construed to limit the scope of the present invention.

EXAMPLE 1

Cell Transfection Assay

Separate 1 mole (80 1 of a 0.0126 M stock solution in chloroform) of N,N-di-n-hexadecyl-N,N-dihydroxyethylammonium bromide (DHDEAB) and 1 mole of the neutral colipid cholesterol (40 1 of a 0.0255 M stock solution in chloroform) were combined in a glass vial. The solvent was evaporated initially by a thin flow of moisture free nitrogen and then under high flow for two minutes and then further dried under vacuum (1 mm Hg) for 6 hours.

The dried lipid film was then hydrated with sterile deionized water (1 ml) overnight (9–10 hours) in room temperature to produce a dispersed suspension. The hydrated mixture was then vortexed for 1 minute and was sonicated in a probe sonicator at a constant 25 W sonic power for 5 minutes. The concentrations of both DHDEAB and cholesterol in the resulting solution obtained after sonication was 1 mM.

For preparation of the transfecting solution, DNA encoding galactosidase (pCH 110 construct as described in Borras et al. *Developmental Biology* 127, 209–219, 1988) was dissolved in DMEM culture medium (GIBCO/BRL No. 12800-017). The resulting solution had a DNA concentration of 454 M (assuming an average molecular weight of 660 Dalton per base pair for nucleotides in the encoding DNA).

A 24 1 aliquot of the sonicated dispersion obtained (containing 1 mM of both cationic lipid and the colipid) was pipetted into separate wells of 96-well plate already containing 51 1 DMEM solution. The resulting 330 M solution (with respect to both the cationic amphiphile and the colipid) was then three fold serially diluted for five times to obtain diluted amphiphile and cholesterol solutions within the range of 330 M –4 M, the volume of each resulting diluted solution being 50 l. To each 50 l resulting diluted solution, 2 l of 454 M DNA solution was added and the mixture was kept stirring for ½ hour at room temperature to allow for the DNA-lipid complexation.

A COS-1 (SV 40 transformed African green monkey kidney, # ATCCCRL 1650, from ATCL, Maryland, U.S.A.) cell line was used for the in vitro assay. The cells were cultured in DMEM media containing 10% fetal bovine serum ("FBS", Sigma F 0392) supplemented with Penicillin, Streptomycin and Kanamycin. Cells were plated into 24-well tissue culture plate to a density of approximately 5–6×1 cells/well and kept for about 12–14 hours until a near confluent (75–80%) pattern had been achieved.

To the DNA-lipid complex volume of 52 1, 350 1 of DMEM was added and mixed thoroughly. The 24-well plates with COS-1 cells were aspirated in order to remove growth medium. The cells were washed once with phosphate buffered saline (PBS). Now to consecutive wells of 24-well plates, 2011 of the DNA-lipid complex was added over the cells and the mixture was incubated for 3 hours in a $CO_2$ incubator. 2001 of 10% FBS containing DMEM was added to each cell well. After a further 20 hour incubation period, the medium was removed and a fresh DMEM with 10% FBS was added. Following a further 24 hours incubation period, cells were assayed for expression of galactosidase and protein.

For protein estimation, the resultant medium was removed from the plates and the cells were were washed with PBS. Lysis buffer (1001 containing 250 mM Tris.HCl, pH 8.0, 0.5% NP40) was added and the cells were lysed for 30 minutes. Lysate was passed through the pipette tip several times to dislodge and dissolve the cell fragments, 2.5 1 of lysate from each well was transferred to a 96-well plate containing 2.5 1 $H_2O$, 25 1 reagent A and 200 1 reagent B from the detergent compatible Bio-Rad protein assay kit (Bio-Rad 500–0116). The plates were read in an Elisa reader (Molecular Devices, Vmax) with a 650 nm filter. Proteins standard curve was also constructed by the same procedure using bovine serum albumin as standard.

The level of galactosidase activity in a 501 lysate was measured by adding to 501 of 2×gal mixture containing 1.33 mg/ml o-nitrophenyl-D-galactopyranoside (Sigma N1127), 200 mM sodium phosphate pH 7.15 and 200 mM magnesium sulfate. The o-nitrophenyl-D-galactopyranoside, following enzymatic hydrolysis at 37° C. gave a yellow colour which was detected and measured by a plate reader equipped with a 405 nm filter. A galactosidase (Sigma No. G6512) standard calibration graph was constructed for calculating the amount of galactosidase in each well. Following subtraction of background readings, optical data determined by the plate reader allowed determination of galactosidase activity and protein content for each well. The results were finally summarized in terms of microunit of galactosidase per microgram of protein content (Reporter gene activity). Representative examples of such reporter gene activities observed with the cationic amphiphiles of the present invention are shown in FIGS. 4–7 of the drawings accompanying this specification.

The above described example is only an illustration with pCH 110. We have performed similar experiments with pCMV gal (GIBCO BRL, Gaithersberg, U.S.A.) & pGFPNI (Clone Tech, Palo Alto, U.S.A.) and we have obtained similar reporter gene activities.

EXAMPLE 2

Procedure for the simultaneous preparation of N,N-di-n-hexadecyl-N,N-dihydroxyethylammonium bromide (DHDEAB), amphiphile No 1 and N-n-hexadecyl-N,N-dihydroxyethylammonium bromide (HDEAB), amphiphile No. 2

A mixture of diethanolamine (1 g, 9.5 mmol), n-hexadecyl bromide (2.9 g, 9.5 mmol) and potassium carbonate (1.44 g, 10.5 mmol) was refluxed in methanol for 48 hours. Methanol was removed on a rotatory evaporator and the residue was extracted with chloroform (3×100 ml). The combined chloroform extract was filtered repeatedly (3 times) to remove potassium carbonate. Chloroform was removed from the filtrate on a rotary evaporator and the residue was taken in 50 ml 80:15:5 (v/v) acetonitrile: ethyl acetate:methanol. One equivalent of n-hexadecyl bromide (2.9 g, 9.5 mmol) was added and the mixture was refluxed for 56 hours. At this point, an additional equivalent of potassium carbonate (1.44 g, 10.5 mmol) was added and refluxing was continued for another 30 hours. Finally, one more equivalent of n-hexadecyl bromide (2.9 g, 9.5 mmol) was added and the mixture was refluxed for 24 hours. The solvent was removed on a rotary evaporator and the residue was extracted with chloroform (100 ml). Potassium carbonate was filtered from the chloroform extract and the chloroform was removed on a rotary evaporator. The residue was dissolved in ethyl acetate (30 ml) with the help of little methanol (0.3–0.5 ml) and the resulting solution of the product mixture showed three spots (with $R_f$=0.9, 0.8 and 0.7) on thin layer chromatography (TLC) using 30:70 (v/v) methanol:chloroform as the TLC developing solvent. The solution was kept at 4° C. for 36 hours. The precipitate that appeared at this point was predominantly the compound with $R_f$=0.9 which was further purified by silica gel chromatography using finer than 200 mesh size silica and eluting with 2–5% methanolic (by volume) chloroform. The NMR and HRMS of this column purified product (yield: 470 mg) showed it to be a O-n-hexadecyl derivative of the title amphiphile No 1 that did not show any gene transfection activity. The mother liquor was concentrated and dry packed with 60–120 mesh size silica. The dry packed residue was loaded on a 60–120 mesh size silica column and was eluted first with ethyl acetate and then with chloroform to wash off unreacted n-hexadecyl bromide and diethanolamine. The compounds with $R_f$=0.8 and 0.7 were then isolated as a mixture by changing the eluent to 90:10 (v/v) chloroform:methanol. The isolated product mixture was finally dry packed with finer than 200 mesh size silica and the dry packed mixture was loaded on a finer than 200 mesh size silica column. The title amphiphiles 1 and 2 (with $R_f$=0.8 and 0.7 respectively) were finally isolated in pure forms by eluting the dry-packed column carefully with chloroform containing 2–5 % methanol (by volume). The yields of the purified amphiphile 1 and amphiphile 2 were respectively 8% (500 mg, 0.787 mmol) and 12.7% (500 mg, 1.2 mmol).

$^1$H-NMR of amphiphile 1 (200 MHz, CDCl$_3$): □/ppm= 0.9 [t, 6H, C$\underline{H}_3$—(CH$_2$)$_n$—]; 1.20–1.5 [m, 52H, —(C$\underline{H}_2$)$_{13}$—]; 1.55–1.85 [m, 4H, (HOCH$_2$—CH$_2$)$_2$N$^+$(CH$_2$—C$\underline{H}_2$—)$_2$]; 3.4–3.6 [m, 4H, (HOCH$_2$—CH$_2$)$_2$N$^+$(C$\underline{H}_2$—CH$_2$—)$_2$]; 3.65–3.80 [m, 4H, (HOCH$_2$—C$\underline{H}_2$)$_2$N$^+$(CH$_2$—CH$_2$—)$_2$]; 4.05–4.2 (m, 4H, (HOC$\underline{H}_2$—CH$_2$)$_2$N$^+$(CH$_2$—CH$_2$—)$_2$]; 4.75–4.95(m, 2H, —O$\underline{H}$).

HRMS (FABS) m/z: Calcd (for C$_{36}$H$_{76}$NO$_2$ the 4°-ammonium ion) 554.5876 found 554.5899

$^1$H-NMR of amphiphile 2 (200 MHz,CDCl$_3$) :□/ppm=0.9 [t, 3H, C$\underline{H}_3$—(CH$_2$)$_n$—]; 1.15–1.5 [m, 26H, CH$_3$—(C$\underline{H}_2$)$_{13}$—]; 1.75–1.85 [m, 2H, (HOCH$_2$—CH$_2$)$_2$N$^+$(CH$_2$—C$\underline{H}_2$—)$_2$]; 3.2–3.35 [m, 2H, (HOCH$_2$—CH$_2$)$_2$N$^+$(C$\underline{H}_2$—CH$_2$—CH$_2$—)$_2$[; 3.35–3.5 ]m, 4H, (HOCH$_2$—C$\underline{H}_2$)$_2$N$^+$(CH$_2$—CH$_2$—)$_2$]; 4.0–4.15 [m, 4H, (HOC$\underline{H}_2$—CH$_2$)$_2$N$^+$(CH$_2$—CH$_2$—)$_2$];

HRMS (FABS) m/z: Calcd (for C$_{20}$H$_{44}$NO$_2$ the 4°-ammonium ion) 330.3372 found 330.3346.

EXAMPLE 3

Procedure for preparing N-methyl-N-n-octadecyl-N-oleyl-N-hydroxyethylammonium chloride (MOOHAC), amphiphile No 3.

Step (a). 100 ml dry dichloromethane was cooled to 0° C. and to the cold dichloromethane solution was added 1.9 g of oleyl aldehyde (7.14 mmol), 1.92 g of stearyl amine (7.14 mmol) and 10.9 g of anhydride magnesium sulfate (7.14 mmol). The mixture was kept under stirring for 3 hours while the temperature of the stirred mixture raised gradually from 0° C. to room temperature. The magnesium sulfate was filtered from the reaction mixture and the filtrate was diluted with 50 ml of methanol. The diluted dichloromethane/methanol solution was cooled to 0° C. and to the cold solution, 0.54 g Sodium borohydride (14.0 mmol) was added. The solution was kept stirred for 4 hours during which time the temperature of the reaction mixture gradually raised to room temperature. The reaction mixture was taken in 100 ml chloroform, washed with water (2×100 ml), the chloroform layer was dried over anhydride magnesium sulfate and filtered. Chloroform was removed from the filtrate on a rotary evaporator and column chromatographic (using 60–120 mesh size silica) purification of the residue using 20–50% ethyl acetate in pet-ether as the eluent afforded 2.34 g (64% yield) of the desired intermediate secondary amine, namely, N-oley-N-n-octadecylamine.

Step (b). A mixture of 0.95 g (1.83 mmol) of N-oley-N-n-octadecylamine obtained in step (a) and 0.67 g (1.83 mmol) of 2-bromoethyl-tertbutyl-diphenylsilyl ether [prepared conventionally by the reaction between 2-bromoethanol and tertbutyl-diphenylsilyl chloride in the presence of triethylamine and N,N-dimethylaminopyridine] was refluxed in ethyl acetate in presence of anhydrous potassium carbonate (0.28 g, 2.01 mmol) for 48 hours. The reaction mixture was taken in 100 ml chloroform, washed with water (2×100 ml), dried over anhydrous magnesium sulfate and filtered. Chloroform was removed from the filtrate on a rotary evaporator. Silica gel column chromatographic purification of the resulting residue using 60–120 mesh size silica and 3–4 % ethyl acetate (by volume) in pet-ether as the eluent afforded 0.69 g (47% yield) of the intermediate tertiary amine, namely the O-tertbutyl-diphenylsilyl derivative of N-2-hydroxyethyl-N-oley-N-n-octadecylamine. The tert-bytul-diphenylsilyl protecting group of this intermediate tertiary amine (0.67 g, 0.84 mmol) was conventionally removed by stirring with tetrabutylammonium fluoride (2.1 mmol, 2.1 ml of 1M tetrabutylammonium fluoride solution in tetrahydrofuran) in dry tetrahydrofuran (cooled to 0° C. ) for 4 hours during which the temperature of the reaction mixture gradually raised to room temperature. The usual work-up and silica gel column purification (as described above in detail for isolating pure protected intermediate except that the eluent used in this case was 7–10% ethyl acetate in pet-ether) of the product mixture afforded 0.32 g (67.5% yield) of pure deprotected tertiary amine namely, N-oley-N-n-octadecyl-N-2-hydroxyethylamine.

Step (c). Quaternization of 0.12 g (0.21 mmol) of N-oley-N-n-octadecyl-N-2-hydroxyethylamine obtained in step (b) was carried out in 5 ml of 5:4 chloroform: methanol (v/v) at room temperature for overnight using huge excess of methyl iodide (4 ml). The solvents were removed on a rotary evaporator and silica gel column chromatographic purification of the residue using 60–120 mesh size silica and 3–4% methanol (by volume) in chloroform afforded the quaternary iodide salt of the title amphiplile. Finally, 0.08 g of pure title amphiphile No. 3 in 91.9% yield was obtained by subjecting the quaternized ammonium iodide salt (0.1 g, 0.14 mmol) to repeated (4 times) chloride ion-exchange chromatography. each time using a freshly generated Amberlyst A-26 chloride ion exchange column column and about 80 ml of chloroform as the eluent. All the isolated intermediates gave spectroscopic data in agreement with their assigned structures shown in FIG. 4. Thus, the title amphiphile 3 was prepared in 3 steps with an overall yield of 18.7%.

$^1$HR-NMR of amphiphile 3 (200 MHz, CDCl$_3$): □/ppm= 0.89 [t, 6H, C$\underline{H}_3$—(CH$_2$)$_n$—]; 1.20–1.45 [m, 52H, —(C$\underline{H}_2$)$_{13}$—]; 1.60–1.80 [br, 4H, CH$_3$(HOCH$_2$—CH$_2$)N$^+$(CH$_2$—C$\underline{H}_2$—)$_2$]; 1.90–2.10 (m, 4H, —C$\underline{H}_2$—CH=CH—C$\underline{H}_2$—); 3.35 [s, 3H, C$\underline{H}$(HOCH$_2$—CH$_2$)N$^+$(CH$_2$—CH$_2$—)$_2$)]; 3.41–3.58 [br, 4H, CH$_3$(HOCH$_2$—CH$_2$)N$^+$(C$\underline{H}_2$—CH$_2$—)$_2$]; 3.65–3.80 [br, 2H, CH$_3$(HOCH$_2$—C$\underline{H}_2$)N$^+$(CH$_2$—CH$_2$—)$_2$]; 4.07–4.12 [br, 2H, CH$_3$(HOC$\underline{H}_2$—CH$_2$)N$^+$(CH$_2$—CH$_2$—)$_2$]; 5.32 (m, 2H, —CH$_2$—C$\underline{H}$=C$\underline{H}$—CH$_2$—).

HRMS (FABS) m/z: Calcd (for C$_{39}$H$_{80}$NO, the 4° C.-anmmonium ion) 578.6239, found 578.6233.

EXAMPLE 4

Procedure for preparing N,N,-di[O-hexadecanoyl] hydroxyethyl-N-hydroxyethyl-N-methylammonium bromide (DOHEMAB), amphiphile 5.

Step (a). Di-O-palmitoylation of N-methyldiethanolamine was effected following a published protocol [Tundo et al. *J. Am. Chem. Soc.* 104, 456–461]. Briefly, N-methyldiethanolamine (1 g, 8.39 mmol) was reacted with palmitoyl chloride (5.075 g, 18.5 mmol) in 10 ml dry N,N-dimethylformamide at 0° C. and the temperature was gradually raised to room temperature within a period of 4 hours. The resulting hydrochloride salt of N-methyl-di-O-palmitoylethanolamine was filtered, crystallized from 20 ml of dry ether. Finally, recrystallization from 20 ml 5:15 (v/v) methanol:ethyl acetate afforded 3.8 g of the pure hydrochloride intermediate in 68% yield.

Step (b). The recrystallized hydrochloride salt (200 mg) was stirred for 5 minutes in a dichlorometlhane (10 ml)/1.0 M aqueous NaOH (10 ml) biphasic system. The top aqueous layer was discarded and the lower organic layer was washed with water (2×50 ml), dried over anhydrous sodium sulfate, filtered and dichloromethane was removed on a rotary evaporator. Pure N-methyl-di-O-palmitoylethanolamine (0.14 g, 0.22 mmol, 74.1% yield) was purified from the residue by silica gel column chromatography using 60–120 mesh size silica and 98:2 (v/v) chloroform:methanol as the eluent.

Step (c). Quatemization of N-methyl-di-O-palmitoylethanolamine was effected by reacting the purified tertiary amine (0.14 g, 0.22 mmol) with 1.5 equivalent of neat 2-bromoethanol (0.063 g, 0.34 mmol) at 85° C. for 4 hours. The quaternized title amphiphile salt 5 was crystallized from the residue using 10 ml 2:8 (v/v) benzene: n-pentane. Silica gel column chromatographic purification of the resulting crystal using 60–120 mesh size silica and 4:96 (v/v) methanol:chloroform as the eluent finally afforded 0.04 g of the pure title amphiphile 5 in 16.5 % yield. All the isolated intermediates gave spectroscopic data in agreement with their assigned structures. Thus, the title amphiphile 5 was prepared in 3 steps with an overall yield of 8.3%.

$^1$H-NMR of amphiphile 5 (200 MHz, CDCl$_3$): □/ppm= 0.88 [t, 6H, C$\underline{H}_3$—CH$_2$—C$_{13}$H$_{26}$—]; 1.20–1.40 [m, 48H, —(C$\underline{H}_2$)$_n$—]; 1.50–1.68 [m, 4H, CH$_3$(HOCH$_2$—CH$_2$)N$^+$(CH$_2$—CH$_2$—O—CO—CH$_2$—C$\underline{H}_2$—)$_2$]; 2.21–2.40 [2t, 4H, CH$_3$(HOCH$_2$—CH$_2$)N$^+$(CH$_2$—CH$_2$—O—CO—C$\underline{H}_2$—CH$_2$—)$_2$]; 3.43 [s, 3H, C$\underline{H}_3$(HOCH$_2$—CH$_2$)N$^+$(CH$_2$—CH$_2$—O—CO—CH$_2$—CH$_2$—)$_2$]; 3.50–4.30 [m, 9H, CH$_3$($\underline{H}$OCH$_2$—CH$_2$)N$^+$(C$\underline{H}_2$—CH$_2$—O—CO—CH$_2$—CH$_2$—)$_2$]; 4.51–4.58 [br, t, 4H, CH$_3$(HOCH$_2$—CH$_2$)N$^+$(CH$_2$—C$\underline{H}_2$—O—CO—CH$_2$—CH$_2$—)$_2$].

HRMS (FABS) m/z: Calcd (for C$_{39}$H$_{79}$NO$_5$, the 4°-ammonium ion) 641.5958, found 641.5907.

We claim:

1. A method for intracellular delivery of biologically active molecules, said method comprising administering to a patient at least one biologically active molecule and at least one amphiphile represented by the following structural formula:

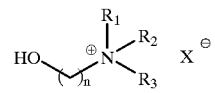

wherein;

n=1, 2, or 3;

R$_1$=H or saturated C$_7$–C$_{20}$ alkyl;

R$_3$=C$_1$–C$_3$ alkyl or a C$_1$–C$_3$ hydroxyalkyl;

R$_2$=saturated C$_7$–C$_{19}$ alkyl or (CH$_2$)$_n$—Z—(C$_7$–C$_{19}$ saturated alkyl);

Z=—CH$_2$—; and

X=either a halogen or a tosylate.

2. A method for intracellular delivery of biologically active molecules, said method comprising administering to a mammal at least one biologically active molecule and at least one amphiphile represented by the following structural formula:

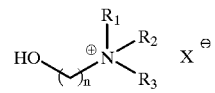

wherein;

n=1, 2, or 3;

R$_1$=H or saturated C$_7$–C$_{20}$ alkyl;

R$_3$=C$_1$–C$_3$ alkyl or an C$_1$–C$_3$ hydroxyalkyl;

R$_2$=saturated C$_7$–C$_{19}$ alkyl or (CH$_2$)$_n$—Z—(C$_7$–C$_{19}$ saturated alkyl);

Z=—CH$_2$—; and

X=either a halogen or a tosylate.

3. A method for intracellular delivery of biologically active molecules, said method comprising delivering to a cell at least one biologically active molecule and at least one amphiphile represented by the following structural formula:

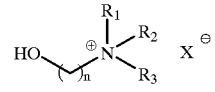

wherein;

n=1, 2, or 3;

R$_1$=H or saturated C$_7$–C$_{20}$ alkyl;

R$_3$=C$_1$–C$_3$ alkyl or an C$_1$–C$_3$ hydroxyalkyl;

R$_2$=saturated C$_7$–C$_{19}$ alkyl or (CH$_2$)$_n$—Z—(C$_7$–C$_{19}$ saturated alkyl);

Z=—CH$_2$—; and

X=either a halogen or a tosylate.

4. A composition comprising:

at least one biologically active molecule; and at least one amphiphile represented by the following structural formula:

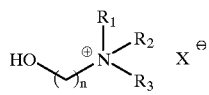

wherein;
n=1, 2, or 3;
$R_1$=H or saturated $C_7$–$C_{20}$ alkyl;
$R_3$=$C_1$–$C_3$ alkyl or an $C_1$–$C_3$ hydroxyalkyl;
$R_2$=saturated $C_7$–$C_{19}$ alkyl or $(CH_2)_n$—Z—($C_7$–$C_{19}$ saturated alkyl);
Z=—$CH_2$—; and
X=either a halogen or a tosylate.

5. A composition comprising:
at least one biologically active molecule;
at least one co-lipid; and
at least one amphiphile represented by the following structural formula:

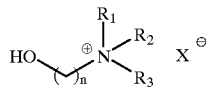

wherein;
n=1, 2, or 3;
$R_1$=H or saturated $C_7$–$C_{20}$ alkyl;
$R_3$=$C_1$–$C_3$ alkyl or an $C_1$–$C_3$ hydroxyalkyl;
$R_2$=saturated $C_7$–$C_{19}$ alkyl or $(CH_2)_n$—Z—($C_7$–$C_{19}$ saturated alkyl);
Z=—$CH_2$— or; and
X=either a halogen or a tosylate.

6. The method for intracellular delivery of biologically active molecules of claim 2 or claim 3 where said amphiphile is represented by the following structural formula:

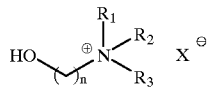

wherein;
n=1, 2, or 3;
$R_1$=H or a saturated alkyl;
$R_3$=$C_1$–$C_3$ hydroxyalkyl;
$R_2$=$C_7$—$C_{19}$ saturated alkyl or $(CH_2)_n$—Z—($C_7$–$C_{19}$ saturated alkyl);
Z=—$CH_2$—, and
X=either a halogen or a tosylate.

7. The method for intracellular delivery of biologically active molecules of claim 2 or claim 3 where said amphiphile is represented by the following structural formula:

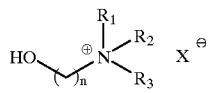

wherein;
n=2;
$R_1$=H or saturated $C_8$–$C_{20}$ alkyl;
$R_3$=hydroxyethyl;
$R_2$=$C_7$–$C_{19}$ saturated alkyl; and
X=Cl or Br.

8. The method for intracellular delivery of biologically active molecules of claim 2 or claim 3 where said amphiphile is N,N-di-n-hexadecyl-N,N-dihydroxyethylammoniuin bromide.

9. The method for intracellular delivery of biologically active molecules of claim 2 or claim 3 where said amphiphile is represented by the following structural formula:

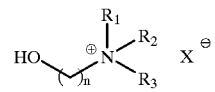

wherein;
n=2;
$R_1$=is selected from n-$C_{14}H_{29}$ to n-$C_{20}H_{41}$;
$R_3$=2-hydroxyethyl;
$R_2$=n-$C_{11}H_{23}$ to n-$C_{17}H_{35}$;
X=Cl or Br.

10. The method for intracellular delivery of biologically active molecules of claim 2 or claim 3 where said amphiphile is represented by the following structural formula:

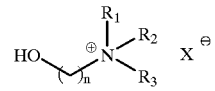

wherein;
n=1, 2; or 3;
$R_1$=$C_8$–$C_{20}$ saturated alkyl;
$R_3$=$C_1$–$C_3$ alkyl;
$R_2$=$C_7$–$C_{19}$ saturated alkyl or $(CH_2)_n$—Z—($C_7$–$C_{19}$ saturated alkyl);
Z=methylene;
X=halogen or tosylate.

11. The method for intracellular delivery of biologically active molecules of claim 2 or claim 3 where said amphiphile is represented by the following structural formula:

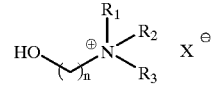

wherein;
n=2;
$R_1$=$C_8$–$C_{20}$ alkyl;
$R_3$=alkyl comprising a $C_1$–$C_3$;
$R_2$=$C_7$–$C_{19}$ saturated alkyl; and
X=Cl or Br.

12. The method for intracellular delivery of biologically active molecules of claim 2 or claim 3 where said amphiphile is N,N-di-n-octadecyl-N-methyl-N-dihydroxyethylammonium chloride.

13. The method for intracellular delivery of biologically active molecules of claim 2 or claim 3 where said amphiphile is represented by the following structural formula:

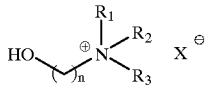

wherein;
n=2;
$R_1$=n-$C_{14}H_{29}$ to n-$C_{20}H_{41}$;
$R_3$=methyl or ethyl;
$R_2$=n-$C_{11}H_{23}$ to n-$C_{12}H_{25}$ or $(CH_2)_n$—Z—($C_7$–$C_{19}$ saturated alkyl);
Z=—$CH_2$—, and
X=Cl or Br.

14. The method for intracellular delivery of biologically active molecules of claim 2 or claim 3 where said amphiphile is N-n-hexadecyl-N,N-dihyddroxyethyl-ammonium bromide.

15. The method for intracellular delivery of biologically active molecules of claim 2 or claim 3 where said amphiphile is represented by the following structrual formula:

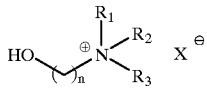

wherein;
n=2;
$R_1$=H;
$R_3$=2-hydroxyethyl;
$R_2$=n-$C_{11}H_{23}$ to n-$C_{17}H_{35}$ or $(CH_2)_n$—Z—($C_7$–$C_{19}$ saturated alkyl);
Z=—$CH_2$—, and
X=Br.

16. The composition intracellular delivery of biologically active molecules of claim 4 or claim 5 where said amphiphile is represented by the following structural formula:

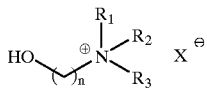

wherein;
n=1, 2, or 3;
$R_1$=H or a saturated alkyl group;
$R_3$=$C_1$–$C_3$ hydroxyalkyl;
$R_2$=$C_7$–$C_{19}$ saturated alkyl or $(CH_2)_n$—Z—($C_7$–$C_{19}$ saturated alkyl);
Z=—$CH_2$—, and
X=either a halogen or a tosylate.

17. The composition for intracellular delivery of biologically active molecules of claim 4 or claim 5 where said amphiphile is represented by the following structural formula:

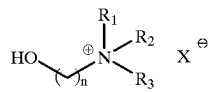

wherein;
n=2;
$R_1$=H or saturated $C_8$–$C_{20}$ alkyl;
$R_3$=hydroxyethyl;
$R_2$=$C_7$–$C_{19}$ saturated alkyl; and
X=Cl or Br.

18. The composition for intracellular delivery of biologically active molecules of claim 4 or claim 5 where said amphiphile is N,N-di-n-hexadecyl-N,N-dihydroxyethylammonium bromide.

19. The composition for intracellular delivery of biologically active molecules of claim 4 or claim 5 where said amphiphile is represented by the following structural formula:

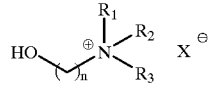

wherein;
n=2;
$R_1$=is selected from n-$C_{14}H_{29}$ to n-$C_{20}H_{41}$;
$R_3$=2-hydroxyethyl;
$R_2$=n-$C_{11}H_{23}$ to n-$C_{17}H_{35}$;
X=Cl or Br.

20. The composition for intracellular delivery of biologically active molecules of claim 4 or claim 5 where said amphiphile is represented by the following structural formula:

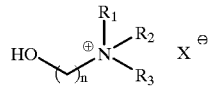

wherein;
n=1, 2; or 3;
$R_1$=$C_8$–$C_{20}$ saturated alkyl;
$R_3$=$C_1$–$C_3$ alkyl;
$R_2$=$C_7$–$C_{19}$ saturated alkyl or $(CH_2)_n$—Z—($C_7$–$C_{19}$ saturated alkyl);
Z=methylene;
X=halogen or tosylate.

21. The composition for intracellular delivery of biologically active molecules of claim 4 or claim 5 where said amphiphile is represented by the following structural formula:

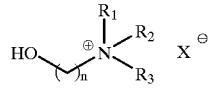

wherein;
n=2;
$R_1$=$C_8$–$C_{20}$ alkyl;

$R_3$=alkyl comprising a $C_1$–$C_3$ group;
$R_2$=$C_7$–$C_{19}$ saturated alkyl; and
X=Cl or Br.

22. The composition for intracellular delivery of biologically active molecules of claim 4 or claim 5 where said amphiphile is N,N-di-n-octadecyl-N-methyl-N-dihydroxyethylammonium chloride.

23. The composition for intracellular delivery of biologically active molecules of claim 4 or claim 5 where said amphiphile is represented by the following structural formula:

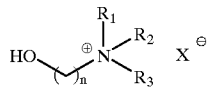

wherein;
n=2;
$R_1$=n-$C_{14}H_{29}$ to n-$C_{20}H_{41}$;
$R_3$=methyl or ethyl;
$R_2$=n-$C_{11}H_{23}$ to n-$C_{12}H_{25}$ or $(CH_2)_n$—Z—($C_7$–$C_{19}$ saturated alkyl);
Z=—$CH_2$—, and
X=Cl or Br.

24. The composition for intracellular delivery of biologically active molecules of claim 4 or claim 5 where said amphiphile is N-n-hexadecyl-N,N-dihydroxyethyl-ammonium bromide.

25. The composition intracellular delivery of biologically active molecules of claim 4 or claim 5 where said amphiphile is represented by the following structural formula:

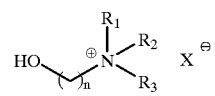

wherein;
n=2;
$R_1$=H;
$R_3$=2-hydroxyethyl;
$R_2$=n-$C_{11}H_{23}$ to n-$C_{17}H_{35}$ or $(CH_2)_n$—Z—($C_7$–$C_{19}$ saturated alkyl);
Z=—$CH_2$—, and
X=Br.

* * * * *

UNITED STATES PATENT AND TRADEMARK OFFICE
CERTIFICATE OF CORRECTION

PATENT NO.   : 6,346,516 B1
DATED        : February 12, 2002
INVENTOR(S)  : Rajkumar Banerjee et al.

It is certified that error appears in the above-identified patent and that said Letters Patent is hereby corrected as shown below:

Column 18,
Line 40, "1, 2; or 3;" should read -- 1, 2, or 3; --.

Column 19,
Line 23, "dihyddroxyethyl-" should read -- dihydroxyethyl --.
Line 44, "composition intracellular" should read -- composition for intracellular --.

Column 20,
Line 47, "1, 2; or 3;" should read -- 1, 2, and 3; --.

Column 21,
Line 5, "composition intracellular" should read -- composition for intracelluar --.

Signed and Sealed this

Eighteenth Day of June, 2002

Attest:

Attesting Officer

JAMES E. ROGAN
*Director of the United States Patent and Trademark Office*